United States Patent [19]

Sugerman et al.

[11] Patent Number: 4,512,928

[45] Date of Patent: Apr. 23, 1985

[54] PYROPHOSPHATO TITANATE ADDUCTS

[75] Inventors: Gerald Sugerman, Allendale, N.J.; Salvatore J. Monte, Staten Island, N.Y.

[73] Assignee: Kenrich Petrochemicals, Inc., Bayonne, N.J.

[21] Appl. No.: 506,385

[22] Filed: Jun. 21, 1983

Related U.S. Application Data

[62] Division of Ser. No. 362,091, Mar. 26, 1982, Pat. No. 4,417,009, which is a division of Ser. No. 224,055, Jan. 12, 1981, Pat. No. 4,338,220, which is a division of Ser. No. 70,907, Aug. 29, 1979, Pat. No. 4,277,415.

[51] Int. Cl.$^3$ .............................................. C11C 3/02
[52] U.S. Cl. ................................ 260/410.9 R; 560/234
[58] Field of Search ................. 260/410.9 E; 560/234

[56] References Cited

U.S. PATENT DOCUMENTS 4,080,353  3/1978  Monte et al. ............... 260/429.5 X
4,083,860  4/1978  Ruf .............................. 260/429.5 X
4,137,183  1/1979  Caspari ...................... 260/429.5 X Primary Examiner—Helen M. S. Sneed
Attorney, Agent, or Firm—Bert J. Lewen

[57] ABSTRACT

Adducts of tetrasubstituted pyrophosphato titanates and/or amines, having the formula $$X_c Ti[OP(O)(OR^1)OP(O)(OR^2)OR^3]_{4-c}$$

$$(NR^4 R^5 R^6)_d [P(OR^7)(OR^8)(OR^9)]_e,$$

are useful in improving the physical and chemical properties of many filled resins.

6 Claims, No Drawings

PYROPHOSPHATO TITANATE ADDUCTS

This is a division of application Ser. No. 362,091, filed Mar. 26, 1982, which in turn is a division of U.S. Pat. No. 4,417,009 prior application Ser. No. 224,055 filed Jan. 12, 1981, now U.S. Pat. No. 4,338,220, which in turn is a division of prior application Ser. No. 070,907 filed Aug. 29, 1979, now U.S. Pat. No. 4,277,415.

BACKGROUND OF THE INVENTION

The present invention relates to adducts of tetrasubstituted pyrophosphato titanates with phosphites and/or amines. The pyrophosphato titanate adducts of the present invention are useful in controlling the viscosity, flow and the conductivity of many filled resins. They improve the physical and chemical properties of many filled resins thereby permitting more valuable and more stringent usage with maintained ease of processing. They also serve as acid catalysts in various applications and inhibit water/salt caused corrosion in treated substrates.

The titanates of the present invention differ from the pyrophosphate titanates disclosed in U.S. Pat. Nos. 4,122,062 and 4,087,402 primarily by the controlled reactivity of the titanates presently mentioned which permits long term storage of said titanates and of the treated filler/pigment resin at ambient to moderately elevated temperatures, and a very specific initiation of functional rates of activity to occur at controlled temperatures depending upon the specific adduct ligand employed. Other advantages conferred upon pyrophosphate titanates by adduction as taught in the present invention include a substantially reduced tendency for such adducts to crystallize as compared to their non-adducted analogs thereby permitting greater ease of dispersion in more vehicles and decreased acidity. In addition, many of the nitrogeneous adducts are water soluble, thereby permitting use of aqueous vehicles in conjunction with fillers and pigments which were heretofore incompatible in water as well as the incorporation of water as a diluent in organic systems which were previously incapable of accepting significant water dilution.

SUMMARY OF THE INVENTION

The pyrophosphato titanate adducts of the present invention may be represented by the following formula:

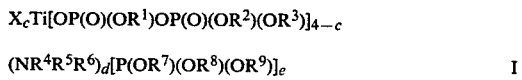

$$X_c Ti[OP(O)(OR^1)OP(O)(OR^2)(OR^3)]_{4-c}$$
$$(NR^4R^5R^6)_d[P(OR^7)(OR^8)(OR^9)]_e \quad \text{I}$$

In formula I, c is 1 or 2; d is 0, 1 or 2; and e is 0, 1 or 2, with the proviso that d plus e must be 1 or 2. When c is 2, X is either RO— or a group which taken together with the Ti to which it is attached forms a ring having the following Formula VI:

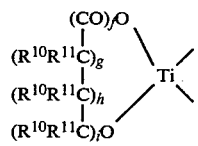

when c is 1, however, X must be RO—. In Formula VI, each of f, g, h and i is 0 or 1, with the proviso that at least one of g, h and i is 1 and that the sum of f, g, h and i is 2 or 3. Each R is independently chosen from among 1 to 10 carbon alkyl groups, 3 to 10 carbon alkenyl groups, 7 to 10 carbon aralkyl groups, 2 to 10 carbon oxyalkylene groups and 3 to 10 carbon dioxyalkylene groups. $R^1$, $R^2$, $R^4$, $R^7$, each $R^{10}$ and $R^{11}$ are independently chosen from among hydrogen, 6 to 10 carbon aryl groups, 7 to 20 carbon aralkyl groups, 1 to 20 carbon alkyl groups, 3 to 20 carbon alkenyl groups, 2 to 20 carbon oxyalkylene groups and 3 to 20 carbon oligooxyalkylene groups, except that one and only one of $R^1$ and $R^2$ must be hydrogen. $R^5$, $R^6$, $R^8$ and $R^9$ are independently chosen from the same groups as $R^1$, $R^2$, $R^4$, $R^7$, $R^{10}$ and $R^{11}$ except that $R^5$, $R^6$, $R^8$ and $R^9$ may not be hydrogen. $R^5$ and $R^6$ may also be independently chosen from among 1 to 10 carbon alkyl, 3 to 10 carbon alkenyl, 6 to 10 carbon aryl and 7 to 10 carbon aralkyl groups. These last four groups optionally have from 1 to 3 carboxylate groups or from 1 to 3 carboxamide groups as substituents. Each such substituent may be saturated or unsaturated and have from 1 to 5 carbon atoms. $R^5$ and $R^6$ may also be independently chosen from among 1 to 10 carbon alkanols, 2 to 6 carbon alkadiols or 7 to 10 carbon aralkanols. When aromatic carbons are present in R, $R^2$, $R^4$, $R^7$, $R^{10}$ and $R^{11}$ groups, each of said carbons is optionally substituted by 1 or 2 independently selected halogen atoms (for example, fluorine, chlorine, bromine or iodine).

The present invention also relates to the use of such adducts for treating particulate fillers, including pigments, the compositions of fillers and the aforesaid adducts with thermoplastics, thermosets and coating or casting resins, and the use of such adducts in conjunction with coating and casting resin compositions in the absence of particulates.

DESCRIPTION OF THE PREFERRED EMBODIMENTS

The aforementioned alkyl and alkenyl groups, and alkyl and alkylene portions of the other aforementioned groups may be straight chain, branched chain or cyclic. Examples of alkyl groups are methyl, hexyl and decyl. Examples of cyclic alkyl groups are cyclohexyl and cyclooctyl. Allyl and crotyl are examples of alkenyl groups. Oxyalkylene groups are exemplified by methoxymethyl and methoxyethyl. Aralkyl groups are exemplified by benzyl and beta naphthyl methyl. Examples of $R^1$, $R^2$, $R^3$, $R^4$, $R^5$, $R^6$, $R^7$, $R^8$, $R^9$, $R^{10}$ and $R^{11}$ are likewise numerous. In addition to the above mentioned groups cited as examples of R, these groups are also exemplified by higher carbon analogs of the above such as octadecatrienyl and 2,4,6-trimethyl-1-cyclohexyl as well as by naphthyl and biphenyl aralkyl groups such as 2-phenethyl, 2-chloro,4-bromophenyl or naphthyl. In addition to the above, $R^5$ and $R^6$ are exemplified by such groups as 3-methacrylpropyl, and 2-acrylamidoethyl hydroxy methyl and dihydroxy octyl.

The inorganic materials that may be treated with the titanate adducts of the present invention may be particulate or fibrous and of any shape or particle size, the surfaces of which are reactive with the hydrolyzable group of the organo-titanium compound by means of hydroxyl groups, or absorbed water, or both. Examples of such reactive inorganic materials are the metal oxides of zinc, magnesium, lead, and calcium and aluminum, iron filings and turnings, and sulfur. Examples of inorganic materials that are reinforcing materials are metals, clay, carbon black, calcium carbonate, barium sulfate, silica, mica, glass and asbestos. Examples of such inorganic materials that are pigments are titanium dioxide, iron oxides, zinc chromate and ultramarine blue. As a practical matter, it is preferable that the particle size of the inorganic material should not be greater than 1 mm, preferably from 1 micron to 500 microns.

It is imperative that the titanate adduct be properly admixed with the inorganic material so as to permit the surface of the latter to react sufficiently. The optimum amount of the titanate to be used is dependent on the effect to be achieved, the available surface area of and the bonded water in the inorganic material.

Reaction is facilitated by admixing under the proper conditions. Optimum results depend on the properties of the titanate, namely, whether it is a liquid or solid, and its decomposition and flash point. The particle size, the geometry of the particles, the specific gravity and the chemical composition, among other things, must be considered. Additionally, the treated inorganic material must be thoroughly admixed with the polymeric medium. The appropriate mixing conditions depend on the type of polymer, for example, whether it is thermoplastic or thermosetting, and its chemical structure, as will be readily understood by those skilled in the art.

Where the inorganic material is pretreated with the titanate adduct, it may be admixed in any convenient type of intensive mixer, such as a Henschel (trademark of Prodex) or Hobart (trademark of Hobart Corporation) mixer of a Waring (trademark of Dynamics Corporation of America) blender. Even hand mixing may be employed. The optimum time and temperature is determined so as to obtain substantial reaction between the inorganic material and the organic titanate. Mixing is performed under conditions at which the organic titanate is in the liquid phase, at temperatures below the decomposition temperature. While it is desirable that the bulk of the hydrolyzable groups be reacted in this step, this is not essential where the materials are later admixed with a polymer, since substantial completion of the reaction may take place in this latter mixing step.

Polymer processing, e.g., high shear mixing, is generally performed at a temperature well above the second order transition temperature of the polymer, preferably at a temperature where the polymer will have a low melt viscosity. For example, low density polyethylene is best processed at a temperature range of 177° to 232° C.; high density polyethylene from 204° to 246° C.; and polystyrene from 232° to 260° C. Temperatures for mixing other polymers are known to those skilled in the art and may be determined by reference to existing literature. A variety of mixing equipment may be used, e.g., two-roll mills, Banbury (trademark of Farrel Corporation) mixers, double concentric screws, counter or corotating twin screws and ZSK type of Werner and Pfleiderer (trademark of Werner & Pfleiderer) and Bussex (trademark of Bussex Corp.) mixers.

When the titanate adduct and the inorganic materials are dry-blended, through mixing and/or reaction is not readily achieved and the reaction may be substantially completed when the treated filler is admixed with the polymer. In this latter step, the titanate adduct may also react with the polymeric material if one or more of the groups on the titanate adduct is reactive with the polymer.

The ratio of pyrophosphato titanate to adducting agents is preferably 1:1 or 1:2, with the latter ratio most preferred. Each adducting ligand may be the same or different. In those formulations in which either the phosphorus based or the nitrogen based adducting agents are different, the product obtained is usually a mix of possible adducts including mixed as well as identical ligands. In those adducts wherein combinations of nitrogen and phosphorus are employed, it is often possible by control of stoichiometry and mode of addition to maintain an almost complete dispersity of product, if so desired.

When used in conjunction with particulates, the adducts of the present invention are employed at levels of at least 0.01 parts by weight, preferably from 0.1 to 5 parts by weight, and most preferably from 0.2 to 2 parts by weight, per 100 parts by weight of inorganic solid. The portion of adduct actually chosen by one skilled in the art is a function of the inorganic solid, its surface area and the particular titanium adduct selected. Upon reaction between the titanate and the surface of the inorganic solid, the titanate becomes chemically bonded to at least a portion of the inorganic solid, thereby modifying the surface considerably. The modified inorganic solid is generally far more easily dispersed in organic media than is the untreated solid. For treatment purposes, the titanate may be added to a suitable vehicle, such as water or a resin to be filld depending upon the investigator's desire and/or the nature of the titanate being employed. This addition is followed by appropriate shear to create an adequate level of dispersion. The treated particulate, in addition to being more effectively coated, will almost certainly have substantially valuable additional properties, such as the ability to act as a catalyst, improved adhesion to substrate, and/or the ability to activate a cross-linking agent in appropriate vehicle systems, primarily due to the availability or organofunctionality added by attached titanate molecules.

The amount of treated filler added to a resin generally ranges from about 1% to about 15% for a pigment and from about 1% to about 500% for an extender (all percentages are % by weight based on the weight of the resin). A wide variety of resins may be filled with fillers that are treated with the titanate adducts of the present invention. Examples of such resins are coating resins, casting resins, thermoplastic resins and thermosetting resins. Examples of all of the foregoing may be found in the reference Modern Plastics Encyclopedia.

In many instances, it is advantageous to dilute the titanate with an appropriately compatible fluid before the titanate is introduced into resin vehicles or before it is mixed with an inorganic particulate. Examples of appropriate inert fluids are aromatic hydrocarbons, ethers and glycol ethers. In many applications involving the use of nitrogeneous adducts of pyrophosphato titanates, water may also be utilized as a solubilizing inert vehicle, particularly in applications involving subsequent use in aqueous systems, such as latex products.

The compounds of the present invention may be prepared by numerous routes. Among the synthetic routes which have proven successful are the addition of appropriate phosphites (Formula II) and/or amines (Formula III) to the corresponding pyrophosphato titanates (Formula IV) described in U.S. Pat. Nos. 4,122,062 and 4,087,402. The reaction of tetraalkyl titanate phosphite adducts (Formula V), preparation of which is described in U.S. Pat. No. 4,080,353 with addition of an appropriate pyrophosphate, an amine and/or a phosphite and/or a chelating agent may also be utilized, as may processes employing titanium tetrachloride in place of tetraalkyl titanates. The aforementioned formulae are shown below:

FORMULA II

P(OR$^7$)(OR$^8$)(OR$^9$)

FORMULA III

NR$^4$R$^5$R$^6$

FORMULA IV

X$_c$Ti[OP(O)(OR$^1$)OP(O)(OR$^2$)(OR$^3$)($_{9-c}$

FORMULA V (RO)$_4$Ti(P;(OR$^7$)(OR$^8$)(OR$^9$)$_d$

In Formulae II, III, IV and V, the various notations and functional groups have the definitions given above for Formula I.

Another synthetic route found useful for the preparation of the phosphite adducts of the present invention wherein the adduct ligands are homogeneous is the reaction of tetraalkyl titanate with an admixture of disubstituted pyrophosphoric acid and the phosphite ligand(s). This last technique is the preferred one for the preparation of mono and di-phosphite adducts of such pyrophosphato titanates. Variations of the aforementioned synthetic routes will be apparent to those skilled in the art.

The preparation of phosphite adducts of corresponding pyrophosphato titanates may be accomplished under adiabatic conditions (since minimal heat evolution occurs) at any convenient temperature between approximately −20° C. and approximately 150° C. The addition of the phosphite to the pyrophosphato titanate in either direct or reverse order of addition will, in general produce minimal visual or thermal indication of reaction. However, typically, a bathochromic shift of the absorption maximum toward, and, occasionally even into the visual absorption range, will generally be observed. Additionally, the melting point will be depressed below that of the corresponding unadducted precursor. Solubility of the resulting titanate in hydrocarbon media will generally be increased at the expense of the dispersibility in water. By contrast, those adducts produced by the addition of appropriately substituted amines to pyrophosphato titanates or their phosphite adducts will generally provide substantial exotherms of formation together with displacement of stoichiometric proportions of phosphite, if present, and will produce products of considerably enhanced water solubility as compared to the parent pyrophosphato titanate. Techniques employing the addition of dibasic pyrophosphates to tetrasubstituted titanate adducts of phosphite and/or amines will also generate substantial exotherms of formation and in both of these latter two synthetic approaches, temperatures should be kept within the range of approximately 0° C. to approximately 150° C. by external cooling in order to minimize product degradation and/or by-product formation. Examples 1 through 4 below, are illustrative of the above mentioned techniques in the order indicated above for the preparation of pyrophosphato organo titanate adducts of the present invention. Subsequent examples 5 through 17 are illustrative of the utility of the materials of the present invention for a variety of applications, such as corrosion control, pigment/filler dispersion, catalyst activity control and impact improvement. Preferred methods of incorporation of the titanate adducts of the present invention into filled resin systems and their uses both in the presence and in the absence of fillers, for purposes other that those listed above are also illustrated.

EXAMPLE 1

Preparation of Di(butyl,methyl)pyrophosphato ethylene titanate di(dioctyl phosphite)

This example illustrates the sequential addition mode of phosphite adduct formation.

206 g of dimethyl acid pyrophosphate (1 mole) and 296 g of dibutyl acid pyrophosphate (1 mole) were charged into a 2 liter stainless steel and glass assembly comprising a mechanically stirred 2 liter glass vessel equipped with a thermometer, addition funnel, and a water cooled jacket. 285 g of tetraisopropyl titanate (1 mole) was added via the addition funnel over a period of 1 hour. Cooling sufficient to prevent the reaction mass temperature from exceeding 150° C. was maintained throughout the addition period. After 20 minutes of further mixing, 62 g of ethylene glycol (1 mole) were added over a period of about 20 minutes, at an addition rate and at a cooling rate such that the temperature of the reaction mass was kept between 42° and 46° C. 612 g dioctyl phosphite (2 moles) were then added, all at once. The resulting mass was transferred to a 2 liter flask equipped for vacuum distillation and was distilled from a water bath to give a pot residue having a boiling point of 80° C. 231 g of isopropyl alcohol (3.85 moles, GLC assay greater than 98%) were recovered as a distillate via liquid nitrogen cooling of volatiles. Product recovery was 1246 g (100% yield). The product was a pale yellow low viscosity liquid which crystallized slowly from a 40% solution in n-hexane at −20° C. to give light amber platelike crystals having a melting point of 48±3° C. Recovery was 1014 g (81%). The omission of byproduct isopropanol removal lowered product recovery on crystallization to 63%, but otherwise gave unchanged results.

EXAMPLE 2

Preparation of Di(butyl, methyl)pyrophosphato ethylene titanate di(dioctyl phosphite)

This example illustrates the preparation of the example adduct in situ.

The procedures, reaction conditions and materials exemplified in Example 1 were employed except that the dioctylphosphite was introduced with the pyrophosphates prior to titanate addition. The nature of the crude product produced and its yield (1248 g, 100%) were essentially unchanged, but this order of addition was found to provide several operating advantages. Among the advantages were lower and more uniform exotherms of tetraisopropyl titanate addition (possibly due to the larger mass in the pot "heat sink", and/or to the more efficient cooling made possible by the reaction mass' considerably lower viscosity) and virtual freedom from the formation of crystalline intermediates of undetermined nature which formed copiously during the procedure given in Example 1, unless the dispersion of tetraisopropyl titanate added was extremely efficient.

It should be noted that other tetraalkyl titanates, e.g., methyl, n-butyl, t-butyl, or sec-octyl may be substituted for the tetraisopropyl titanate used in the illustration. However, the use of n-alkyl titanates frequently results in ligand exchange with the pyrophosphate moiety and may therefore result in complex product mixtures, especially via the procedure outlined in Example 1. Furthermore, the removal of higher boiling by-product alkanols, if desired, usually proved more difficult than the removal of the more volatile lower alkanols. The removal of by-product alcohol is optional and is not required for the preparation of the products of the present invention. Said removal merely facilitates product purification and/or may eliminate side reactions in alcohol sensitive substrates such as polyesters and urethanes and/or may provide decreased product flammability.

EXAMPLE 3

Preparation of Di(butyl,methyl)pyrophosphato, ethylene titanate di(dioctyl phosphite)

Tetraisopropyl titanate di(dioctylphosphite), 901 g (1 mole), was charged to a 2 liter stainless steel vessel equipped with an efficient agitator and external cooling. Temperature was maintained at or below 45° C. during the sequential addition of 206 g (1 mole) of dimethyl acid pyrophosphate followed by 296 g (1 mole) of dibutyl acid pryophosphate over a period of approximately one hour each. Ethylene glycol 62 g (1 mole) was then added. The reaction mixture was then transferred to a Pyrex (trademark of Corning Glass for heat resistant borosilicate glass) glass system equipped for simple vacuum distillation and was distilled to give 1238 g (99% yield) of pale yellow oil having a boiling point of greater than 90° C. which slowly crystallized to produce a white waxy crystalline mass having a melting point of 49±4° C.

This procedure was not as satisfactory as that of Example 1, because it suffered from the formation of localized gels during pyrophosphate addition. These gels made mixing difficult.

EXAMPLE 4

Numerous examples of chelated pyrophosphato titanate adducts prepared via the procedure given in Examples 1 to 3 are given in Table 1. Each titanate adduct is identified by a symbol in the extreme left hand column that similarly identifies the adduct in the Examples that follow.

TABLE 1

| | Pyrophosphato Titanate Adduct | Method of Preparation | Melting Point °C. | Calculated % P/Found % P |
|---|---|---|---|---|
| (A) | ethylene di(butyl, octyl)pyrophosphato titanate di(trisethylphosphite) | 1,2,3 | <0 | 16.4/16.1 |
| (B) | 1-oxo-1,3-propylene di(bisphenyl)pyrophosphato titanate dilaurylphosphite | 2,3 | 42 ± 5 | 15.0/14.8 |
| (C) | 1-oxo-2-phenylethylene, di(2-chloro-p-cresyl, methyl)pyrophosphato titanate, triphenyl phosphite | 1,2,3 | 54 ± 3 | 11.3/11.2 |
| (D) | neopentenyl, di(bisoctadecyl) pyrophosphato titanate di(butyl, propyl phosphite) | 1,3 | 27 ± 6 | 9.74/9.5 |
| (E) | 1,3 propylene, di(bisoctadecyl) pyrophosphato titanate di(dibenzyl phosphite) | 1 | <0 | 9.26/9.3 |
| (F) | oxoethylene di(butyl, methoxyethoxyethyl) pyrophosphato titanate dimethoxethylphosphite | 1,2 | <0 | 9.46/9.3 |
| (G) | ethylene di(methyl, 11, 14-hexadecadienyl) pyrophosphato titanate di(bismethyl phosphite) | 1,2,3 | 34 ± 6 | 16.2/16.1 |
| (H) | 1,2-propenyl, di bis(2-bromo-3-chloro-4-butylphenyl) pyrophosphato titanate di(bishexadecyl phosphite) | 1,3 | 64 ± 2 | 12.5/12.6 |
| (I) | ethylene di(butyl,methyl) pyrophosphato titanate di(trisethylamine) | 1,2,3 | 73 ± 4 | 16.9/16.8 |
| (J) | oxoethylene di(butyl, octyl) pyrophosphato titanate 2-dimethylaminoisobutanol | 1 | 42 ± 5 | 13.3/12.9 |
| (K) | ethylene di(bisoctyl)pyrophosphato titanate di(3-dimethylaminopropylmethacrylamide | 1,3 | 82 ± 4 | 9.65/9.9 |
| (L) | benzylethylene di(phenyl, lauryl) pyrophosphate titanate di(ethylaminoethyl acrylate | 1 | 76 ± 4 | 9.57/9.7 |
| (M) | ethylene, di(butyl,methyl) pyrophosphato titanate di(bisoctyl) phosphite | 1 | not isolated* | |
| (N) | oxoethylene di(butyl, octyl)pyrophosphato titanate diphenyl phosphite | 1 | not isolated* | |
| (O) | 2-methyl-2,4-butenyl di(di-p-chlorobenzyl)pyrophosphato titanate di(butoxyethyl,methyl phosphite | 1 | not isolated* | |
| (P) | oxoethylene, di(benzyl, 2-pentenyl)pyrophosphato titanate di(2-dimethylamino) isobutanol | 1,2 | not isolated* | |
| (Q) | 2,3-butenyl di(bis-4-methoxyphenyl)pyrophosphate titanate diethylamine | 1 | not isolated* | |
| (R) | 2,3-dimethyl-2,3-butenyl di(bis- | 1 | not isolated* | |

TABLE 1-continued

| | Pyrophosphato Titanate Adduct | Method of Preparation | Melting Point °C. | Calculated % P/Found % P |
|---|---|---|---|---|
| | methyl)pyrophosphato titanate triethylamine, dibutyl phosphite | | | |
| (S) | oxoethylene di(p-bromobenzyl) pyrophosphato titanate methyl-aminoethanol | 1 | not isolated* | |
| (T) | 1-oxoprop-1,3-enyl di(butoxy-methoxyethyl, isobutyl)pyro-phosphato titanate di(bistridecyl) phosphite | 1 | not isolated* | |
| (U) | methoxyethylene di(bispropyl) pyrophosphate titanate di propylamino ethyl methacrylate | 1 | not isolated* | |
| (V) | isopropyl, tri(butyl, methyl) pyrophosphato titanate di(bis-octyl phosphite) | 1,2,3 | <0 | 17.0/16.8 |
| (W) | isopropyl, tri(bisoctyl)pyro-phosphato titanate triethanol-amine | 1,2, | 16 ± 5 | 12.9/12.8 |
| (X) | isooctyl, tri(bismethyl)pyro-phosphato titanate tripropyl phosphite | 1,2,3 | not isolated* | |
| (Y) | ethoxytriglycolyl, tri(4-bromo-phenyl,methyl)pyrophosphato titanate di(methoxyethyl) phosphite | 1 | 14 ± 6 | 15.3/15.1 |
| (Z) | 4-ethoxybenzyl tri(di-alphanaph-thyl) pyrophosphato titanate di (di-ethylaminoethyl(methacrylate) | 1 | 64 ± 5 | 10.4/10.1 |
| (AA) | t-butyl,tri(bisbutyl) pyro-phosphato titanate tri-methyl phosphite, dimethylaminoethanol | 1 | 12 ± 4 | 17.2/17.0 |
| (AB) | methyl, tri(bis-4-chlorophenyl) pyrophosphato titanate dioctyl phosphite, dimethylaminoethyl formamide | 1 | 48 ± 3 | 15.8/15.5 |
| (AC) | allyl, tri(allyl, methyl)pyro-phosphato titanate trimethyl phosphite, dioctyl phosphite | 1,3 | 23 ± 3 | 20.2/19.9 |
| (AD) | (2,2-diallyloxymethyl)ethyl tri(bisbutyl)pyrophosphato titanate di(trisphenyl phosphite) | 1,2 | 38 ± 4 | 11.9/11.7 |
| (AE) | 1-(2-butenyl)tri(methyl, octyl) pyrophosphato titanate, tri-ethylamine, dioctyl phosphite | 1 | 31 ± 3 | 13.1/12.9 |

*by product alcohol not removed, reaction mixture used as such.

EXAMPLE 5

This example illustrates the utility of various titanate adducts of the present invention as corrosion retardants.

Xylene degreased 20 mil panels of cold rolled steel were dip coated with a 1 weight percent solution of additive in toluene followed by a toluene wash and were then oven dried at 150° C. in a nitrogen atmosphere. The dried panels were cooled, weighed, subjected to 100 hours of 100% humidity at 40° C. exposure in an environmental cabinet, re-dried, cooled, and re-weighed. The corrosion rate in mills per year was calculated from the following equation:

Corrosion rate = (weight loss/panel weight) (20 mils) (8670 hours/year/100 hours)

The results of a study of selected examples of the titanates of the present invention are given in Table 2.

TABLE 2

| Adduct | Indicated Corrosion Rate (mils/yr) | % of Control |
|---|---|---|
| None (control) | 172 | 100 |
| A | 38 | 22 |
| B | 26 | 15 |
| C | 69 | 40 |
| D | 81 | 47 |
| E | 24 | 14 |
| F | 13 | 8 |
| G | 32 | 19 |
| H | 19 | 11 |
| I | 20 | 12 |
| J | 31 | 18 |
| K | 38 | 22 |
| L | 35 | 20 |
| X | 17 | 10 |
| Y | 20 | 12 |
| AB | 26 | 15 |
| AC | 18 | 10 |
| AD | 41 | 24 |
| AE | 38 | 22 |

In each instance, the materials of the present invention improved humidity resistance of cold rolled steel by at least two-fold and in the case of the F material, the improvement was twelve-fold.

EXAMPLE 6

Titanate adducts M through U, identified above, were compounded into an alkyl-melamine baking enamel having a brown color as indicated below. The resultant formulations were each oven baked at 100° C.

for a period adequate to provide a film pencil hardness (Society of Coatings Technology Test) of F-H at 1.3±0.2 mils dry film thickness. The results of this study are given in Table 3.

The following materials were premixed, on a high shear disperser, at ambient temperature for fifteen minutes:

| Material | Kilograms | Liters |
|---|---|---|
| soya alkyd short oil, Cook #S-157-A-2 (trademark of Cook Paint and Varnish Co.) | 172 | 174 |
| pyrophosphato titanate adduct | 0.397 | 0.33 |
| titanium dioxide, DuPont #R-960 (trademark of E.I. DuPont de Nemours, Co.) | 21 | 5.08 |
| magnesium silicate | 32 | 12.0 |
| lamp black | 0.9 | 0.512 |
| red iron oxide | 3.2 | 0.648 |
| yellow iron oxide | 15 | 3.72 |
| bentonite clay | 1.1 | 0.633 |
| fumed silica | 1.1 | 0.523 |
| soya lecithin | 1.4 | 1.42 |

Tetraoctyltitanate di(dioctyl)phosphite (0.188 kilograms, 0.20 liters) was added to the above mixture and the mixture was further mixed on a sand mill until the particle size was Hegman 6.5 grind guage. The resulting blend was added to the following Material Letdown Solution and was mixed at ambient temperature.

| Material Letdown Solution | Kilograms | Liters |
|---|---|---|
| xylene | 41.8 | 48.5 |
| Butyl Cellosolve (trademark of Union Carbide Corporation) | 10.2 | 11 |
| triethylamine | 2.0 | 2.73 |
| n-butanol | 0.90 | 1.12 |
| 50% melamine formaldehyde resin, Cargil #2218 (trademark of Cargill Inc.) | 74.5 | 76 |
| 6% Cobalt naphthenate | 0.90 | 0.95 |

The resulting paint composition had the following properties:

| weight per liter | 1.05 |
|---|---|
| viscosity (#2 Zahn ± 6 sec.) | 28.0 |
| volume solids (%) | 32.0 |
| weight solids (%) | 49.0 |
| thickness dry film | 1.0–1.75 |
| pencil hardness | F-H |
| gloss (±5°) | 55.0 |
| letdown solution to grind ratio | 5:1 |

The bake time at 93° C. required to achieve specification hardness was determined for several titanate adducts of the present invention. The results are shown in Table 3.

TABLE 3

| Pyrophosphato Titanate Adduct Employed | Bake Time at 93° C. Time required to achieve specification hardness (+2 minutes) |
|---|---|
| None (control) | 117 |
| M | 43 |
| N | 41 |
| O | 57 |
| P | 84 |
| F | 21 |
| Q | 39 |
| R | 48 |

TABLE 3-continued

| Pyrophosphato Titanate Adduct Employed | Bake Time at 93° C. Time required to achieve specification hardness (+2 minutes) |
|---|---|
| S | 83 |
| T | 42 |
| U | 38 |

The reduction in bake time required in order to achieve specification properties is clearly shown to be substantial for all members of the class tested. A considerable reduction in cost results from the savings in both time and energy expended during baking.

EXAMPLE 7

This example illustrates the utility of certain pyrophosphato titanate adducts in the simultaneous control of viscosity and pot life of polyester casting resins.

Polyester resin composites were prepared by thoroughly admixing in the following order, 100 g of polyester resin (#30001, trademark of Reichhold Chemical Co.), 0.5 g of pyrophosphate titanate adduct, 100 g of talc (#42, trademark of Englehard Mineral & Chemical Co.), and 1 g of 6% cobalt naphthenate. The resultant dispersions were deaerated by mixing in vacuo to eliminate variable air entrainment. The viscosities of the dispersions were then measured employing a Brookfield RVF viscosimeter (trademark of Brookfield Corp., Stoughton, Mass.). Thereafter, 0.5 g of methyl ethyl ketone peroxide was added to 100 g aliquots of deaerated dispersion and pot life was measured (time to achieve 2 million cps viscosity) at 21° C. The results are given in Table 4.

TABLE 4

| Adduct Employed | Viscosity of Composite (thousands of poise) | Minutes |
|---|---|---|
| None | 2.7 | 33 |
| N | 1.6 | 109 |
| O | 1.3 | 127 |
| F | 0.8 | 18 |
| T | 1.4 | 142 |
| U | 0.6 | 14 |
| V | 3.7 | 37 |
| W | 5.2 | 35 |

The data show that the phosphite adducts N, O and T retard the increase of viscosity due to premature gellation, thereby providing substantially increased useful working pot life, whereas the unsaturated nitrogen based adducts F and U act as accelerators, useful where rapid cure is desired. Furthermore, all of the adducts tested, other than V and W, provided the bonus of lower composite viscosities useful in many low energy application situations. Adducts V and W acted as thixotropes without material effect on pot life, a characteristic not shared by conventional thixotropes such as fumed silica and asbestos which, normally, markedly slow peroxide cures.

EXAMPLE 8

This example illustrates the use of various pyrophosphato titanate adducts to improve the scrubbability of a latex coating.

Test batches of latex paint were prepared by mixing 25 g of titanium dioxide (DuPont #R931, trademark of E. I. DuPont de Nemours) in 20 g of ethylene glycol monobutyl ether containing 0.25 g of pyrophosphato titanate adduct on a high shear disperser (at constant torque) to a Hegman grind gauge of minus 6. This was followed by letdown (dilution) with 100 g of acrylic latex (Ucar 4550, trademark of Union Carbide Corp.) Test panels were then prepared as 3 mil wet (about 2 mil dry) drawdowns on toluene degreased mild steel and the resultant films were dried at 25° C. for 48 hours prior to scrub testing. The scrub tester employed was a ⅛" wide, 10 micron silica impregnated phenolic grinding wheel rotated at 10 RPM. Grinding was continued in each case until magnetic dust was detected. Results are given in Table 5.

TABLE 5

| Adduct | Grind Time (minutes) Required for −6(Hegman) | Scrub Cycles |
|---|---|---|
| Control | 22 | 38 |
| B | 14 | 57 |
| C | 12 | 83 |
| D | 13 | 71 |
| E | 9 | 46 |
| Q | 14 | 143 |
| G | 15 | 71 |
| H | 12 | 62 |
| I | 14 | 49 |
| J | 13 | 53 |
| K | 15 | 168 |

These data show that the use of the adducts of the present invention markedly improved both the grinding efficacy and the scrub resistance in those formulations in which they were employed and that in several cases (C, F and K) the improvements in scrub resistance were twofold or higher.

EXAMPLE 9

This example illustrates the utility of pyrophosphato titanium adducts of the present invention for the improvement of epoxy polyamide coatings.

The coating components A and B were prepared separately by mixing the ingredients listed in Tables 6A and 6B, respectively, in the order indicated at 33° C. to 45° C., using a Cowles dissolver (trademark of Moorhouse Cowles Co.). Components A and B were admixed at ambient temperature using the same equipment. Q-panels (trademark of Q-Panel Corp.) of cold rolled steel were coated with portions of the test coating to provide a film one mil dry thickness. The coatings were aged for one week at ambient temperature before testing. Test results ae given in Table 6C.

TABLE 6A

| | Component A | |
|---|---|---|
| Ingredient | BLSC Control Parts by weight | Silica System Parts by weight |
| epoxy resin (Araldite 571CX80, trademark of Ciba-Geigy Corp.) | 210 | 210 |
| basic lead silicochromate (BLSC) | 480 | None |
| titanium dioxide | 30 | 30 |
| red iron oxide | 15 | 15 |
| fumed silica | 6.4 | 6.4 |
| talc | 235 | 235 |
| amorphous silica | None | 400 |
| xylene | 193 | 193 |
| diacetone alcohol | 96 | 96 |
| urea formaldehyde resin (Beetle 216-8, trademark of America Cyanamid Corp.) | 10.5 | 10.5 |
| chelated pyrophosphato titanate adduct | None | 3.3 |

TABLE 6A-continued

| | Component A | |
|---|---|---|
| Ingredient | BLSC Control Parts by weight | Silica System Parts by weight |
| parts by weight | 1276 | 1199 |

TABLE 6B

| | Component B | |
|---|---|---|
| Ingredient | BLSC Control Parts by weight | Silica System Parts by weight |
| polyamide curative (Araldite 820, trademark of Ciba-Geigy Corp.) | 105 | 105 |
| xylene | 24 | 24 |
| butanol | 12 | 12 |
| parts by weight | 141 | 141 |

The cost per gallon of the Component A BLSC Control was $1.35; the cost per gallon of the Component A titanate adduct formulation was about $0.66.

TABLE 6C

| Adduct | Initial viscosity KU* | Four Month viscosity KU | Rusting after 1000 hour salt fog exposure at 27° C. | Stripped panel rusting after 500 hours, 100% humidity at 27° C. |
|---|---|---|---|---|
| BLSC (Control) | 192 | 216 | M (moderate) | S (severe) |
| B | 112 | 126 | Sl (slight) | Sl |
| C | 103 | 104 | Sl | M |
| D | 106 | 118 | Sl | Sl |
| E | 102 | 104 | Sl | Sl |
| Q | 116 | 109 | Sl | M |
| G | 109 | 111 | M | M |
| H | 113 | 115 | Sl | Sl |
| I | 96 | 100 | M | Sl |
| J | 101 | 107 | Sl | Sl |

*Krebs units

Note that as compared with the BLSC Control, each of the pyrophosphato titanate adducts of the present invention provided improved protection against corrosion at a cost considerably lower than that of the BLSC Control without the employment of environmentally damaging heavy metals as required by the best previously available technology. Also demonstrated are the massive viscosity reduction achieved via the use of the products of the present invention as a major contributing capability to the functional utility of the silica system since control viscosity would otherwise prevent effective application coverage.

EXAMPLE 10

This example illustrates the utility of pyrophosphato titanium adducts of the present invention as adhesion promoters for polymer laminates.

The titanate adducts listed in Table 7 below were compounded into virgin low density polyethylene (LDPE). Thirty mil sheets of the LDPE were extrusion laminated onto preformed 50 ml Surlin (trademark of DuPont de Nemours for metalated polyolefin) ionomer sheets at 107° C., employing a 24:1 vented National Plastics Machinery (trademark) extruder. The peel strength of each laminate was measured with a constant speed motor and a strain gauge at 27° C. after 24 hours at ambient temperature and pressure. The results are given below in Table 7. The formulations contained 0.2 weight percent of the indicated chelated pyrophosphato titanium adduct on LDPE.

TABLE 7

| Adduct | Peel Strength, kg/cm$^2$ |
|---|---|
| Control | 4.8 |
| A | 9.0 |
| B | 19 |
| C | 20 |
| D | 17 |
| E | 20 |
| G | 17 |
| H | 16 |
| I | 24 |
| Z | 13 |

Note that in each instance, the use of the adducts improved peel strength (bonding) between the dissimilar polymer layers.

EXAMPLE 11

This example illustrates the utility of pyrophosphato titanium adducts of the present invention in enhancing the tensile and elongation properties of cellulosics (cross-linked low density polyethylene filled with cotton linters).

One hundred parts by weight of low density cross-linkable polyethylene, 20 parts cotton linters (chopped to 20–45 micron length, 0.5 parts dicumyl peroxide and 0.2 parts of pyrophosphato titanate adduct were compounded on a two roll mill at 93±6° C. (all parts given are parts by weight). Samples were then press cured at 149° C. for 20 minutes. The samples were equilibrated at 21° C. for 24 hours prior to testing on an Instron (trademark of Instron Corporation) tensile tester at an extention rate of 0.2 inches/min. The results are given below in Table 8.

TABLE 8

| Adduct | Tensile Strength, kg/cm$^2$ | Elongation at Break, % |
|---|---|---|
| Control | 6.11 × 10$^3$ | 80 |
| A | 6.53 × 10$^3$ | 90 |
| D | 7.95 × 10$^3$ | 170 |
| Q | 10.9 × 10$^3$ | 230 |
| K | 8.80 × 10$^3$ | 210 |

EXAMPLE 12

This examples illustrates the use of pyrophosphato titanate adducts as viscosity control agents and/or dispersants in dissimilar media (for example, water and mineral oil).

In each instance, the indicated titanate was precoated at 0.5 weight percent on HiSil 223 (trademark of PPG Industries) in a household type blender prior to dispersion in the liquid vehicle (water or mineral oil) at 70 weight percent HiSil using a Hochmeyer disperser (trademark of Hochmeyer Corp.). The resulting dispersions were evaluated at 27° C. using a Brookfield RVF viscometer (trademark). The results are given in Table 9.

TABLE 9

| Additive | Aqueous dispersion viscosity MCPS (10$^3$ centipoise) | Mineral Oil dispersion viscosity MCPS |
|---|---|---|
| Control | 152 | 23 |
| A | 130 | 28 |
| B | 37 | 56 |
| C | 52 | 72 |
| D | 168 | 22 |
| E | 182 | 18 |

TABLE 9-continued

| Additive | Aqueous dispersion viscosity MCPS (10$^3$ centipoise) | Mineral Oil dispersion viscosity MCPS |
|---|---|---|
| Q | 154 | 21 |
| G | 172 | 19 |
| H | 41 | 62 |
| I | 227 | separates rapidly |
| J | 47 | 62 |
| K | 164 | 18 |
| Z | 194 | 17 |
| Y | 184 | 18 |
| AD | 171 | |

This example demonstrates the wide range of viscosity control available in vehicles as diverse as water and mineral oil via the employment of small proportions of pyrophosphato titanium adducts in conjunction with a single (silica) particulate.

EXAMPLE 13

This example illustrates the utiity of pyrophosphato titanium adducts as promoters of conductivity in metal filled polymer composites. In each instance, the metal indicated was precoated with the specified adduct by admixture in a household type blender prior to incorporation into the polymer base on a laboratory two roll mill. The formulations were press cured and formed as 6 inch × 6 inch × 100 mil sheets for 20 minutes at 170° C. and stress relieved at 27° C. for 24 hours, prior to evaluation. Resistivities were measured using a field effect transistor type ohmeter equipped with a decade runup box of 10$^1$ to 10$^9$ ohms range on a through the sample basis. The results are given in Table 10 (Tables 10a, 10b and 10c).

TABLE 10

TABLE 10a

Formulation (in parts by weight): nickel (1 micron nominal powder, manufactured by Potter Industries), 87.5; Geon 103EP (trademark of B.F. Goodrich Co. for PVC resin), 7; dioctyl phthalate, 4.5; mixed barium, cadmium and zinc oxalate stabilizer, 0.5; epoxidized soybean oil, 0.5; pyrophosphato titanate adduct, 0.25.

| Adduct | Resistance ohm/cm Nickel | Resistance ohm/cm Tin |
|---|---|---|
| Control | 1.3 × 10$^6$ | 3.9 × 10$^6$ |
| B | 16 | 6.2 × 10$^2$ |
| C | 28 | 4.8 × 10$^2$ |
| Q | 45 | 87 |
| E | 63 | 1.1 × 10$^2$ |
| K | 1.1 × 10$^2$ | 96 |

TABLE 10b

Formulation (in parts by weight): nickel (1 micron nominal powder), 75; SWS (trademark of Stauffer Chemical Co. for silicone resin), 24; dicumyl peroxide, 1.0; pyrophosphato titanium adduct, 0.25.

| Adducts | Resistance ohm/cm |
|---|---|
| Control | 1.6 × 10$^8$ |
| B | 2.0 × 10$^4$ |
| C | 1.4 × 10$^4$ |
| E | 4.7 × 10$^2$ |
| Q | 6 × 10$^2$ |
| K | 1.7 × 10$^2$ |
| Y | 5.7 × 10$^5$ |
| Z | 6.2 × 10$^3$ |
| AA | 4.1 × 10$^3$ |
| AB | 8.1 × 10$^1$ |
| AD | 6.2 × 10$^2$ |
| AE | 3.8 × 10$^2$ |

TABLE 10c

Formulation (in parts by weight): Viton E430 (trademark of E.I. duPont de Nemours for fluoroelastomer), 24; calcium hydroxide powder, regent grade (manufactured by J.T. Baker Chemical Company), 1.28; nickel (1 micron nominal powder), 75; pyrophosphato titanium adduct, 0.25.

| Adduct | Resistance ohm/cm |
| --- | --- |
| Control | $9 \times 10^8$ |
| B | $5 \times 10^5$ |
| C | $7 \times 10^4$ |
| E | $1.8 \times 10^2$ |
| Q | 38 |
| K | 61 |
| F | $6.1 \times 10^6$ |
| M | $5 \times 10^3$ |
| P | $8 \times 10^3$ |
| AB | $3.4 \times 10^2$ |

In each and every instance the use of pyrophosphato titanate adduct provided for substantial conductivity enhancement versus the control, despite the gross variation in polymer binders employed; (i.e. the silicone and Viton (trademark) are grossly differing thermosets, and the PVC is a thermoplastic).

EXAMPLE 14

This example illustrates the use of selected pryophosphato titanium adducts as insulation value enhancers in hard clay filled flexible polyvinyl chloride.

SP-33 Clay (trademark of Burgess Pigment Co.), 20 parts by weight; dioctyl phthalate, 50; and pyrophosphato titanium adduct 0.01; were admixed in a household type blender. The resulting mixture was added to polyvinyl chloride resin (Geon 103EP, trademark of B. F. Goodrich Co.), 100; epoxidized soybean oil, 3; powdered lead diphthalate, 3; and stearic acid, 0.3, all quantities are in parts by weight. The mix was compounded on a laboratory two-roll mill at 135° C. and press-formed for 10 minutes at 160° C. prior to evaluation of resistance of a sheet having a cross-section of about 100 mils by employing a mehohm Bridge coupled to a $10^4$–$10^5$ ohm decade box assembly. The results are shown in Table 11.

TABLE 11

| Adduct | Resistance ohms/cm |
| --- | --- |
| Control | $5 \times 10^{12}$ |
| B | $2 \times 10^{13}$ |
| C | $3 \times 10^{13}$ |
| D | $8 \times 10^{12}$ |
| Q | $7 \times 10^{12}$ |
| J | $1 \times 10^{13}$ |

These data show that significant resistivity increases result from the employment of pyrophosphato titanate adducts in vinyl based insulation.

EXAMPLE 15

This example illustrates the advantages in terms of shelf stability resulting from the adduction of pyrophosphato titanates with certain types of amines and/or phosphites.

Test formulations containing 40 weight percent Bakelite CK-1634 phenolic resin (trademark of Union Carbide Corp.) and 10 weight percent of powdered coal (Carbofil #1—Shamokin Filler Co.), together with 0.2 weight percent of pyrophosphato titanate (as shown) in xylene were coated on aluminium Q-pannels (trademark of Q-Pannel Corp.) to a wet film thickness of 5 mils and placed in a 150° C. forced draft oven until the resultant film showed a pencil hardness of 3 H. A second sample of each formulation was shelf aged in a closed container, at 25±3° C. to determine package stability. The test results are shown in Table 12

TABLE 12

| Pryophosphato Titanate | Shelf Life (days)[1] | Cure Time Min. |
| --- | --- | --- |
| Control (none) | 60 ± 3 | 25 ± 3 |
| A | 55 ± 5 | 16 ± 2 |
| non-adducted A[2] | 22 ± 2 | 15 ± 2 |
| B | >120 | 14 ± 2 |
| non-adducted B | 20 ± 3 | 15 ± 2 |
| J | >120 | 17 ± 2 |
| non-adducted J (same as A) | 20 ± 3 | 16 ± 2 |
| K | >120 | 20 ± 2 |
| non-adducted K | 28 ± 3 | 19 ± 2 |
| Q | <120 | 16 ± 2 |
| non-adducted Q (same as A) | 22 ± 3 | 15 ± 2 |
| AA | 74 ± 5 | 11 ± 2 |
| non-adducted AA | 18 ± 3 | 10 ± 2 |
| AE | 82 ± 5 | 12 ± 2 |
| non-adducted AE | 16 ± 4 | 12 ± 2 |

[1]Time to 100% Brookfield (trademark) viscosity increase
[2]Prepared as disclosed in U.S. Pat. No. 4,122,062 or 4,087,402

This example shows that while both adducted and non-adducted pyrophosphato titanate decrease cure time with consequent reduction in energy requirements when employed in conjunction with phenolic resins, the non-adducted analogs negatively effect formulation shelf life whereas their adducted analogs either effect shelf life positively or negligibly compared to the control. This example also shows that the choice of adducting agent also has a substantial effect on the properties of the resulting adduct.

EXAMPLE 16

This example shows the advantages of appropriate adduction of pyrophosphato titanates for purposes of melting point depression and ease of dispersion. One gram of the specified adducts of the present invention and, separately, their non-adducted analogs were added to separate 200 mil portions of water. 100 grams of Optiwhite Calcined Clay (trademark of Burgess Corp.) was then dispersed at 30±5° C. using a Hochmeyer disperser and the viscosity of each dispersion measured immediately and after boiling for two hours at 30±1° C. using a Brookfield RVF viscometer (trademark of Brookfield Corp.). The results are shown in Table 13.

TABLE 13

| Pyrophosphato Titanate Employed | Initial 30° C. viscosity (cps) | Boiled dispersion 30° C. viscosity (cps) |
| --- | --- | --- |
| Control | $4.3 \times 10^5$ | $>10^7$ |
| I | $6.7 \times 10^3$ | $>10^7$ |
| non-adducted I | $4.1 \times 10^5$ | $>10^7$ |
| J | $3.9 \times 10^3$ | $5.2 \times 10^4$ |
| non-adducted J | $4.5 \times 10^5$ | $>10^7$ |
| K | $6.3 \times 10^4$ | $4.7 \times 10^4$ |
| non-adducted K | $5.0 \times 10^5$ | $>10^7$ |
| L | $3.9 \times 10^3$ | $8.4 \times 10^3$ |
| non-adducted L | $4.0 \times 10^5$ | $>10^7$ |
| W | $6.1 \times 10^3$ | $>10^7$ |
| non-adducted W | $4.2 \times 10^5$ | $>10^7$ |
| Z | $4.8 \times 10^5$ | $5.2 \times 10^5$ |
| non-adducted Z | $4.5 \times 10^5$ | $>10^7$ |
| AB | $2.9 \times 10^2$ | $>10^7$ |
| non-adducted AB | $4.5 \times 10^5$ | $>10^7$ |
| AE | $8.2 \times 10^4$ | $9.5 \times 10^5$ |
| non-adducted AE | $4.1 \times 10^5$ | $>10^7$ |

This example shows the pyrophosphato titanate adducts of the present invention may be utilized to achieve controlled viscosity reduction of aqueous clay dispersions at ambient temperature with or without controlled distillate(s) was performed by gas liquid chromatography results are given in Table 15.

TABLE 15

| Catalyst Employed | % Yield Byproduct Methyl Acetate | % Recovery Ethyl Acetate | % Yield Methyl Propionate | % Recovery Ethyl Propionate | % Recovery Methyl Butyrate |
|---|---|---|---|---|---|
| Sulfuric Acid | 97 | 2 | <1 | 95 | <1 |
| Aluminum Chloride | 94 | 5 | 4 | 97 | <1 |
| B | 13 | 85 | 84 | 13 | 3 |
| Non adducted B | 89 | 9 | 8 | 90 | 3 |
| H | 7 | 91 | 90 | 8 | 1 |
| Non adducted H | 91 | 8 | 5 | 92 | 2 |
| I | <1 | 99+ | 94 | 5 | 3 |
| Non adducted I | 87 | 11 | 10 | 88 | 2 |
| J | 2 | 96 | 93 | 5 | 2 |
| Non adducted J | 94 | 4 | 5 | 95 | 1 |

*aAll numerical data in mole %.* viscosity lowering after boiling whereas their non-adducted analogs give essentially negligible response in comparable formulations.

EXAMPLE 17

This example shows the utility of adduction of pyrophosphato titanates with amines of Formula III and/or phosphites of Formula II with respect to melting point reduction and with respect to solubility enhancement in selected media.

The indicated phosphato titanates, prepared according to the procedures described in U.S. Pat. Nos. 4,122,062 or 4,087,402, were converted to the indicated adducts via the procedure outlined in Example 1 and solubility (as weight percent) at 25±3° C. was measured in n-hexane (Hexane sol.). Melting points of the phosphato titanate were determined before and after adduction. The results are given in Table 14.

TABLE 14

| Pyrophosphato non-adducted Titanate | Melting Point °C. | Hexane sol. wt. % | Pyrophosphato Titanate adduct | Melting Point °C. | Hexane sol. wt. % |
|---|---|---|---|---|---|
| I | dec 182 | <0.5 | I | 73 ± 4 | 7 |
| V | 171–174 | <0.5 | V | <0 | >25 |
| AA | 158–161 | 1 | AA | 12 ± 4 | >25 |
| AC | 179–184 | <0.5 | AC | 23 ± 3 | >25 |
| AE | 129–134 | 3 | AE | 31 ± 3 | 12 |

This example shows the improvement in hexane solubility and melting point lowering effected upon prior art phosphato titanates via the practice of adduction as described in the present invention.

EXAMPLE 18

This example shows the utility of pyrophosphato titanate adducts as thermally activated catalysts in the controlled interconversion of esters, i.e., the transesterification of ethyl propionate with methyl butyrate in solutions containing ethyl acetate.

In a 2 liter pyrex flask equipped with facilities for mechanical agitation, pot and head thermometers, inert gas inlet, fractionating column (30 theoretical plates), automatic reflux-takeoff assembly, vacuum receivers, external heat and vacuum sources was placed 3M each of ethyl (acetate, ethyl propionate and methyl butyrate, together with 1.0 g of the indicated catalyst. Vacuum and reflux ratios were adjusted to 25 mm and 25:1, respectively, and the pot contents distilled to recover 97±1% of the feed overhead. Analysis of the Note that both conventional acid catalysts and non-adducted pyrophosphato titanates, when employed in the above system, produce substantial proportions of byproduct methyl acetate due to preferential volatilization of same once formed, whereas the adducts of the instant invention, having little catalytic activity until temperatures in excess of 50° C., permitted recovery by vacuum distillation of the bulk of the ethyl acetate prior to onset of catalytic transesterification.

I claim:

1. A method of transesterifying esters which comprises adding to the reaction medium a catalytic amount of a compound having the formula

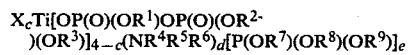

$$X_c Ti[OP(O)(OR^1)OP(O)(OR^{2-})(OR^3)]_{4-c}(NR^4R^5R^6)_d[P(OR^7)(OR^8)(OR^9)]_e$$

wherein c is 1 or 2; d is 0, 1 or 2; e is 0, 1 or 2; with the proviso that d plus e must be 1 or 2; with the proviso that if c is 1, X must be RO—; and with the proviso that when c is 2, X is either RO— or a group which taken together with the Ti to which it is attached forms a ring having the formula

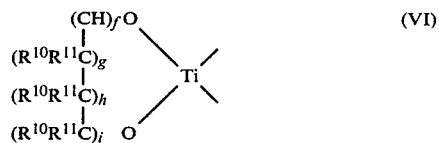

wherein each of f, g, h and i is 0 or 1, with the proviso that at least one of g, h and i is 1 and that the sum of f, g, h and i is 2 or 3; and wherein each R is independently selected from $C_1$ to $C_{10}$ alkyl, $C_3$ to $C_{10}$ alkenyl, $C_7$ to $C_{10}$ dioxyalkylene; $R^1$, $R^2$, $R^4$, $R^7$, each $R^{10}$ and each $R^{11}$ are independently selected from hydrogen, $C_6$ to $C_{10}$ aryl, $C_7$ to $C_{20}$ aralkyl, $C_1$ to $C_{20}$ alkyl, $C_3$ to $C_{20}$ alkenyl, $C_2$ to $C_{20}$ oxyalkylene and $C_3$ to $C_{20}$ oligooxyalkylene, with the proviso that one and only one of $R^1$ and $R^2$ is hydrogen; $R^5$, $R^6$, $R^8$ and $R^9$ are independently selected from the same groups as are $R^1$, $R^2$, $R^4$, $R^7$, each $R^{10}$ and each $R^{11}$, except that $R^5$, $R^6$, $R^8$ and $R^9$ may not be hydrogen, and, in addition, $R^5$ and $R^6$ are independently selected from $C_1$ to $C_{10}$ alkanol, $C_2$ to $C_6$ alkanediol, $C_7$ to $C_{10}$ aralkanol, substituted and unsubstituted $C_1$ to $C_{10}$ alkyl, substituted and unsubstituted $C_3$ to $C_{10}$ alkenyl, substituted and unsubstituted $C_6$ to $C_{10}$ aryl, substituted and unsubstituted $C_7$ to $C_{10}$ aralkyl, these last four groups being optionally substituted with 1 to 3 carboxylate groups or from 1 to 3 carboxamide groups, each such carboxylate group and each such carboxamide group being saturated or unsaturated and having from 1 to 5 carbon atoms; with the proviso that when aromatic carbons are present in any one of R, $R^2$, $R^4$, $R^7$, $R^{10}$ or $R^{11}$, each of said carbons is optionally substituted with 1 or 2 independently selected halogen atoms.

2. The method of claim 1, wherein X is RO—.

3. The method of claim 1, wherein c is 2 and wherein two X groups are taken together with the Ti to which they are attached to form a ring having the formula VI of claim 1.

4. The method of claim 1, wherein C is 1.

5. The method of claim 1, wherein d is 0.

6. The method of claim 1, wherein e is 0.

* * * * *